United States Patent [19]

Boisvenue

[11] Patent Number: 4,692,468

[45] Date of Patent: Sep. 8, 1987

[54] CONTROL OF COLONIAL INSECTS EMPLOYING O-PHENYLENEDIAMINES

[75] Inventor: Rudolph J. Boisvenue, Greenfield, Ind.

[73] Assignee: Eli Lilly and Company, Indianapolis, Ind.

[21] Appl. No.: 416,426

[22] Filed: Sep. 9, 1982

Related U.S. Application Data

[63] Continuation of Ser. No. 174,371, Aug. 1, 1980, abandoned.

[51] Int. Cl.$^4$ ...................... A01N 37/18; A01N 47/10
[52] U.S. Cl. .................................... 514/616; 514/485; 514/488; 514/628
[58] Field of Search ................ 424/300, 324; 514/616, 514/628, 485, 488

[56] References Cited

U.S. PATENT DOCUMENTS

| | | | |
|---|---|---|---|
| Re. 29,508 | 1/1978 | O'Doherty | 71/118 |
| 3,557,211 | 1/1971 | Rumanowski | 280/562 |
| 3,989,840 | 11/1976 | O'Doherty | 424/300 |
| 4,011,341 | 3/1977 | O'Doherty | 424/324 |
| 4,108,631 | 8/1978 | O'Doherty | 71/103 |
| 4,122,165 | 10/1978 | Kinzer et al. | 424/84 |

OTHER PUBLICATIONS

Boisvenue et al; Experientia 36, 189 (1980).
Davey et al; Southwestern Entomologist, 4, #4, 311 (Dec. 1979).
Sorenson et al; Insectide and Acaricide Tests, vol. 3, (The Entomological Society of America 1978), entries 260, 265, 267 & 269.
Van Lier et al; Abst. of Society of Toxicology Meeting at Wash. D.C., 3/10/80, "Disposition of a New Ectoparositic Agent in the Rat".
Day, Jr.; Outline of Intended Oral Publ. delivered by Edgar W. Day 1/30/80 to USDA Fire Ant Working Group Meeting at USDA Animal & Plant Health Inspection Service at Gulfport, Miss.
Day, Jr., "Trip Report" regarding presentation to above meeting (R&40).
Day, Jr.; 7/8/80, Outline of Intended Oral Public by Edgar W. Day, to the USDA, Fire Ant Working Group Meeting at USDA Lab., Gainesville, Fla.
Lofgren et al. (II), "Biology and Control of Imported Fire Ants," *Annual Review of Entomology*, 20:1–30 (1975).
Banks et al., "Laboratory and Field Evaluation of Several Organochlorine and Organophosphorus Compounds for Control of Imported Fire Ants", USDA, ARS, Ser. ARS-S-169, 13 pages. (1977).
Williams et al., "Laboratory Studies with Nine Amidinohydrazones, a Promising New Class of Bait Toxicants for Control of Red Imported Fire Ants", *J. Econ. Entomol.* 73:798–802 (1980).
Farm Chemicals, "Will the Fire Ant Continue to Win?" Jul. 1980, pp. 29–31 (received at the Agricultural Library of Eli Lilly and Company on Jul. 25, 1980).
Stringer et al., "Imported Fire Ant Toxic Bait Studies: Evaluation of Toxicants", *J. Econ. Entomol.* 57:941–5 (1964).
Lofgren et al. (I), "Laboratory Test with Candidate Bait Toxicants Against the Imported Fire Ant", USDA ARS 81-14, 25 pages (1967).

*Primary Examiner*—Allen J. Robinson
*Attorney, Agent, or Firm*—Kathleen R. S. Page; Leroy Whitaker

[57] ABSTRACT

This invention is directed to the use of a class of N-(2,2-difluoroalkanoyl)-o-phenylenediamines as an agent for the control of certain colonial insects, i.e., ants and termites.

7 Claims, No Drawings

CONTROL OF COLONIAL INSECTS EMPLOYING O-PHENYLENEDIAMINES

This application is a continuation of application Ser. No. 174,371, filed 8/1/80 and abandoned after the filing of this application.

BRIEF SUMMARY

This invention is directed to the use of a class of N-(2,2-difluoroalkanoyl)-o-phenylenediamines as an agent for the control of certain colonial insects, i.e., ants and termites.

DETAILED DESCRIPTION OF THE INVENTION

The present invention is directed to a method for eradicating a colonial insect colony comprised of insects of the order Hymenoptera, family Formicidae, or the order Isoptera, family Termitidae, which comprises supplying to the colony an effective amount of an active agent, the active agent being one or more compounds of the class of N-(2,2-difluoroalkanoyl)-o-phenylenediamines defined by the following formula:

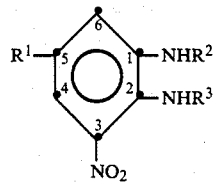

In the above and succeeding formulae, $R^1$ represents
(1) halo,
(2) $CF_3$,
(3) $CF_2H$, or
(4) $CF_2Cl$;
one of $R^2$ and $R^3$ represents a 2,2-difluoroalkanoyl radical of the formula

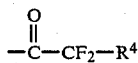

wherein $R^4$ represents
(1) H,
(2) Cl,
(3) F,
(4) difluoromethyl, or
(5) trifluoromethyl;
and the other of $R^2$ and $R^3$ represents
(1) H,
(2) the same 2,2-difluoroalkanoyl radical represented by the first of $R^2$ and $R^3$,
(3) a radical of the formula

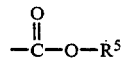

wherein $R^5$ represents lower alkyl of $C_1$-$C_4$ or phenyl,
(4) lower alkanoyl of $C_2$-$C_5$,
(5) benzoyl, or
(6) halogenated lower alkanoyl of $C_2$-$C_5$, subject to the limitation that the alpha position bears at least one substituent selected from the group consisting of hydrogen and halogen of atomic weight from 35 to 127, both inclusive;
subject to the further limitation that when $R^3$ represents a 2,2-difluoroalkanoyl radical, $R^2$ is a group other than H.

Preferred compounds to be employed in the method of the present invention are those of the formula

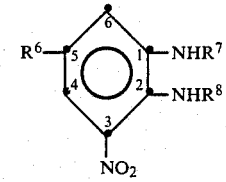

wherein $R^6$ represents chloro or trifluoromethyl; $R^7$ represents a 2,2-difluoroalkanoyl radical as above defined; and $R^8$ represents H or the same 2,2-difluoroalkanoyl radical represented by $R^7$.

The compounds serving as active agent in accordance with the present invention are prepared in known procedures; see the teachings of U.S. Pat. No. 3,557,211 and U.S. Reissue Pat. No. Re. 29,508. In general the compounds are prepared by acylation of an o-phenylenediamine of the formula

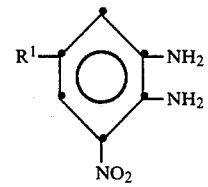

Where $R^2$ is a 2,2-difluoroalkanoyl radical and $R^3$ is H, or where both $R^2$ and $R^3$ are the same 2,2-difluoroalkanoyl radical, the acylating agent is suitably a 2,2-difluoroalkanoyl halide or 2,2-difluoroalkanoic anhydride. Where one of $R^2$ and $R^3$ is a 2,2-difluoroalkanoyl radical and the other is a group other than H or the same 2,2-difluoroalkanoyl radical, the two groups are introduced by sequential acylation reactions. The various acylation reactions are conducted in conventional procedures.

The order Hymenoptera, family Formicidae includes the numerous species of ants. The order Isoptera, family Termitidae includes the various species of termites. Representative species are the following:

Ants (order Hymenoptera, family Formicidae)

Argentine ant-*Iridomyrmex humilis*
Pharaoh ant-*Monomorium pharaonis*
Little black ant-*Monomorium minimum*
Odorous house ant-*Tapinoma sessile*
Thief ant-*Solenopsis molesta*
Cornfield ant-*Lasius alienus*
Pavement ant-*Tetramorium caespitum*
Large yellow ant-*Acanthomyops interjectus*
Small yellow ant-*Acanthomyops claviger*
Black carpenter ant-*Camponotus pennsylvanicus*
Red carpenter ant-*Camponotus ferrugineus*
Florida carpenter ant-*Camponotus abdominalis floridanus*
Brown carpenter ant-*Camponotus castaneus*
Texas leaf-cutting ant-*Atta texana*
Imported fire ant-*Solenopsis geminata*

Black imported fire ant-*Solenopsis richteri*
Red imported fire ant-*Solenopsis invicta*
Southern fire ant-*Solenopsis xyloni*
Leaf cutter ant-*Atta cephalotex*
Leaf cutter ant-*Atta sexdens*
(no common name)-Acromyrmex sp.
Big-headed ant-*Pheidole megacephala*

Termites (order Isoptera, family Termitidae)

Eastern subterranean termite-*Reticulitermes flavipes*
Arid-land subterranean termite-*Reticulitermes tibialis*
Western subterranean termite-*Reticulitermes hesperus*
Common dry-wood termite-*Kalotermes minor*
Southern dry-wood termite-*Kalotermes hubbardi*
Southeastern dry-wood termite-*Kalotermes snyderi*
Dry-wood termite-*Kalotermes schwartzi*
Pacific damp-wood termite-*Zootermopsis angusticollis*
Western dry-wood termite-*Incisitermes minor*
Damp-wood termite-*Paraneotermes simplicornis*
Formosan subterranean termite-*Coptotermes formosanus*
Dry-wood termite-*Criptotermes brevis*
Dry-wood termite-*Criptotermes rospigliosi*
Subterranean termite-*Heterotermes tenuis*
Subterranean termite-*Coptotermes testaceous*
Subterranean termite-*Rhinotermes nasutus*
Tree termite-Nasutitermes sp.
(no common name)-*Ancistrotermes carithorax*
(no common name)-*Microtermes subhyalinus*

The active agent in accordance with the present invention is employed for the control of ants and termites in manners conventional for the particular species.

In the case of ants, the present active agent exhibits the desirable attribute of delayed toxicity following ingestion; therefore, workers carry the active agent back to the hive and share it with other ants, a process known as trophallaxis. Accordingly, the present active agent is supplied in an edible, preferably attractant bait positioned near the colony or colonies. For ant species which infest pastureland or cropland, an edible bait containing the present active agent can be distributed uniformly on the infested land.

The amount of the present active agent which is effective to eradicate an ant colony will vary with factors such as the identity of the ant; the size and number of the colonies; the mode of application; and other factors. For application to pastureland and cropland, good results are generally obtained by application of from 1 to 100 grams/acre and preferably from 1 to 10 grams/acre; such amounts are readily supplied by applying from 0.05 to 10.00 lbs./acre, preferably 1.0 to 5.0 lbs./acre, of a bait comprising 0.05 to 3.00 percent, and preferably 0.1 to 1.0 percent, of the present active agent. For eradication of isolated colonies, good results are generally achieved with baits containing the present active agent at concentrations of 0.01 to 1.00 percent. In general, it is desirable to use a minimum effective amount, to minimize exposure to non-target species. The optimal use for control of fire ants on pastureland and cropland appears to be about 1 lb./acre of a 0.75 percent formulation, to supply about 2 to 4 grams/acre.

Baits containing the present active agent can be prepared in conventional manner. Typically the active agent is dissolved in an oil or fat. The oil or fat can be a vegetable oil such as soybean oil, sesame seed oil, coconut oil, cottonseed oil, safflower oil, peanut oil, or corn oil; or an animal fat such as lard or tallow. Because of its low cost and ready availability, soybean oil is generally preferred. The solution can be supplied as such but is preferably distributed on a carrier such as puffed corn, corncob grits, starch, or the like. In general, any adsorbent material with adequate oil capacity, such as 15 percent or greater, which is not offensive to ants, is acceptable. Pregelled defatted corn grits has been found to be preferable because of its higher oil capacity.

The bait can also include an attractant, such as lecithin or any nutritive substance with particular appeal to the ant species.

In the case of termites, repellency is a more important mode of control, although as shown by the data below, the present active agent exhibits both toxicant and repellent modes of action. Termite control typically takes the form of treating soil surrounding houses and other buildings sought to be protected against termites, although other conventional methods of application can also be employed with the present active agent.

For termite control, the present active agent is formulated in conventional manners. The agent can be dissolved in a solvent or formulated as a water emulsion, for application to soil. For example, the present active agent can be formulated as a wettable powder, e.g.,

| | |
|---|---|
| 3-nitro-5-(trifluoromethyl)-$N^1$—(pentafluoropropionyl)-o-phenylenediamine | 50% |
| Stepanol ME (Stepan Chemical Co. brand of sodium lauryl sulfate) | 5% |
| Polyfon O (an anionic surfactant sold by Westvaco Corporation Polychemicals Dept. and comprising a sodium lignosulfonate) | 5% |
| Zeolex 7 (a sodium silicoaluminate sold by J. M. Huber Corp.) | 5% |
| Bardens clay | 35% | or as an emulsifiable concentrate, e.g.,

| | |
|---|---|
| 3-nitro-5-(trifluoromethyl)-$N^1$—(pentafluoropropionyl)-o-phenylenediamine | 25% |
| acetophenone | 63% |
| Sponto 1003 (a surfactant sold by Witco Chemical, comprising a blend of oil-soluble metal sulfonates and polyoxyethylene ethers) | 12% |

The wettable powder or emulsifiable concentrate can then be dispersed in water to constitute a soil-treating formulation. Similarly, the present active agent can be dissolved in a solvent, including aromatics such as xylene, toluene, and aromatic naphthas; alcohols; esters; and acetonitrile, to constitute a soil-treating formulation. The present active agent generally gives effective termite control when employed in formulations comprising from 0.05 to 1.0% of active agent, applied at standard termite control application rates such as 1 gallon per 5–10 sq. ft. and 1 gallon per $2\frac{1}{2}$–5 lineal ft.

The present active agent is believed to undergo a chemical conversion in warm-blooded animals, illustrated below for the single active agent 3-nitro-5-(trifluoromethyl)-$N^1$-(2,2,3,3-tetrafluoropropionyl)-o-phenylenediamine:

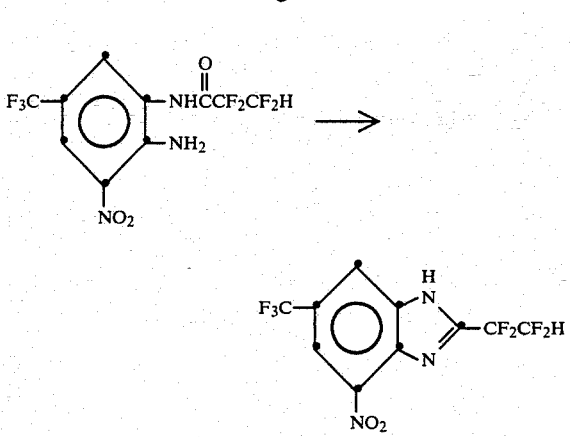

See the Abstract of Society of Toxicology Meeting at Washington, D.C., Mar. 10, 1980, "Disposition of a New Ectoparasitic Agent in the Rat", van Lier et al. The resulting benzimidazole compound, again in warm-blooded animals, is believed to be more toxic. See *Experientia*, 36, (1980), 189 et seq., "Systemic Animal External Parasiticidal Activity of Perfluoroalkylbenzimidazoles and Their Aminoanilide Precursors", by Boisvenue et al.

While the inventor has no data to indicate the fate of the present active agent in ants, it is believed preferable to formulate the present active agent in a manner to minimize conversion to the benzimidazole, since a delayed effect is desired in the control of ants. For example, the formulation should ideally be neutral or slightly acidic.

The practice of the present invention is illustrated by the following examples.

EXAMPLE 1

3-Nitro-5-(trifluoromethyl)-N$^1$-(2,2,3,3-tetrafluoropropionyl)-o-phenylenediamine was evaluated for the control of the red imported fire ant (*Solenopsis invicta*, variety Buren). Four separate tests were conducted, each under laboratory conditions, with worker ants.

Each test was conducted in 30 ml. disposable plastic medicine cups (40 mm internal dimension at the top, tapering to 32 mm internal dimension at the botton, 38 mm high). A hole (6 mm diam.) was drilled through the bottom of each cup and a layer of plaster of Paris and builders' cement (9:1 ratio) was poured over the bottom. The plaster mixture covered the hole and acted as a wick to draw up water when the cup was placed on a wet peat moss bed. (Moisture is necessary to keep the humidity in the cups high and thereby prevent desiccation of the ants. The cement is added to make a hard mixture through which the ants cannot tunnel and escape).

Twenty worker ants from field-collected colonies were placed in each test chamber ca. 24 hours preceding start of the test. This pretreatment holding period allowed time for recovery of the ants from handling and for orientation to the containers.

The candidate compound was dissolved directly in the food material, soybean oil. The toxic solution was offered to the ants on cotton swabs saturated with the material and placed in the test chamber in small vial caps.

The ants were allowed to feed as desired on the toxic bait for 24 hours. After this exposure period, the toxicant was removed from the chamber and the ants remained without food for an additional 24 hours. At the end of this time new vial caps containing cotton swabs saturated with soybean oil were placed in the chamber and left for the remainder of the test period. Knockdown and mortality counts were made at intervals of 1, 2, 3, 6, 8, 10, 13 and 14 days following initial exposure. Each test consists of three replications. Room temperature was maintained at 80±2 F.

Results were as reported in the following table.

TABLE I

| Treatment | No. of tests[a] | Concn. of compound in soybean oil (%) | \multicolumn{7}{c}{Average percent knockdown and kill after indicated no. of days} |
| | | | 1 | 2 | 3 | 6 | 8 | 10 | 14 |
| --- | --- | --- | --- | --- | --- | --- | --- | --- | --- |
| 3-Nitro-5-(trifluoromethyl)-N$^1$—(2,2,3,3-tetrafluoropropionyl)-o-phenylenediamine | 4 | 0.01 | 1 | 1 | 1 | 1 | 7 | 16 | 29 |
| | | .1 | 1 | 6 | 19 | 64 | 82 | 89 | 95 |
| | | 1.0 | 22 | 55 | 86 | 100 | | | |
| Mirex (standard) | 4 | .01 | 0 | 1 | 1 | 7 | 19 | 34 | 58 |
| | | .1 | 1 | 2 | 17 | 66 | 84 | 92 | 100 |
| | | 1.0 | 0 | 57 | 90 | 100 | | | |
| Soybean oil (check) | 4 | | 0 | 2 | 3 | 7 | 9 | 11 | 16 |

[a]Each test consisted of 3 replicates at each concentration, with 20 worker ants per replicate.

EXAMPLES 2-11

A number of the o-phenylenediamines to be employed in accordance with the present invention were also evaluated for activity against the red imported fire ant (*Solenopsis invicta*, variety Buren). The tests were conducted in essentially the same procedures described in the preceding example, with the following minor differences: the peat moss bed was replaced by a saturated 6.4 mm (¼ in. thick) foam pad, and the cups were placed in a tray and covered with a sheet of clean plexiglass to prevent rapid evaporation of the water from the foam pad.

The results were as reported in the following table.

TABLE II

| Treatment | Concn. (%) | \multicolumn{7}{c}{Percent knockdown and mortality after indicated number of days} |
| | | 1 | 2 | 3 | 6 | 8 | 10 | 14 |
| --- | --- | --- | --- | --- | --- | --- | --- | --- |
| 3-Nitro-5-(trifluoromethyl)-N$^1$—(pentafluoropropionyl)-o-phenylenediamine | 0.01 | 0 | 0 | 0 | 2 | 2 | 2 | 7 |
| | 0.1 | 0 | 2 | 3 | 27 | 35 | 43 | 48 |
| | 1.0 | 20 | 57 | 73 | 92 | 93 | 98 | 100 |
| 3-Nitro-5-(trifluoromethyl)-N$^1$,N$^2$—bis-(trifluoroacetyl)-o-phenylenediamine | 0.01 | 0 | 0 | 0 | 0 | 0 | 0 | 7 |
| | 0.1 | 3 | 5 | 12 | 37 | 38 | 42 | 53 |
| | 1.0 | 7 | 23 | 43 | 67 | 73 | 78 | 83 |
| 3-Nitro-5-(trifluoromethyl)-N$^1$—acetyl-N$^2$—(trifluoroacetyl)-o-phenylenediamine | 0.01 | 2 | 3 | 3 | 3 | 7 | 7 | 10 |
| | 0.1 | 0 | 0 | 0 | 5 | 5 | 5 | 18 |
| | 1.0 | 0 | 2 | 2 | 7 | 8 | 12 | 20 |
| 3-Nitro-5-chloro-N$^1$,N$^2$—bis(trifluoroacetyl)-o-phenylenediamine | 0.01 | 3 | 5 | 5 | 5 | 7 | 10 | 17 |
| | 0.1 | 3 | 17 | 33 | 60 | 60 | 63 | 75 |
| | 1.0 | 22 | 72 | 85 | 95 | 95 | 98 | 100 |
| 3-Nitro-5-(trifluoromethyl)-N$^1$—(tri- | 0.01 | 2 | 2 | 2 | 2 | 3 | 5 | 7 |
| | 0.1 | 0 | 0 | 2 | 5 | 8 | 10 | 22 |

TABLE II-continued

| Treatment | Concn. (%) | Percent knockdown and mortality after indicated number of days | | | | | | |
|---|---|---|---|---|---|---|---|---|
| | | 1 | 2 | 3 | 6 | 8 | 10 | 14 |
| chloroacetyl)-$N^2$—(trifluoroacetyl)-o-phenylenediamine | 1.0 | 2 | 25 | 30 | 43 | 45 | 50 | 57 |
| 3-Nitro-5-(trifluoromethyl)-$N^1$,$N^2$—bis-(2,2,3,3-tetrafluoropropionyl)-o-phenylenediamine | 0.01 | 2 | 2 | 2 | 2 | 5 | 10 | 33 |
| | 0.1 | 5 | 27 | 33 | 53 | 55 | 55 | 72 |
| | 1.0 | 45 | 73 | 77 | 88 | 88 | 93 | 98 |
| 3-Nitro-5-(trifluoromethyl)-$N^1$—(methoxycarbonyl)-$N^2$—(difluoroacetyl)-o-phenylenediamine | 0.01 | 2 | 2 | 2 | 3 | 3 | 5 | 5 |
| | 0.1 | 2 | 2 | 3 | 15 | 20 | 22 | 38 |
| | 1.0 | 2 | 23 | 33 | 42 | 42 | 43 | 45 |
| 3-Nitro-5-chloro-$N^1$,$N^2$—bis(2,2,3,3-tetrafluoropropionyl)-o-phenylenediamine | 0.01 | 5 | 5 | 7 | 8 | 8 | 8 | 8 |
| | 0.1 | 0 | 2 | 5 | 15 | 15 | 17 | 17 |
| | 1.0 | 15 | 45 | 55 | 63 | 67 | 67 | 73 |
| 3-Nitro-5-(trifluoromethyl)-$N^1$—acetyl-$N^2$—(2,2,3,3-tetrafluoropropionyl)-o-phenylenediamine | 0.01 | 3 | 7 | 7 | 12 | 17 | 20 | 23 |
| | 0.1 | 2 | 3 | 7 | 8 | 13 | 23 | 23 |
| | 1.0 | 0 | 8 | 28 | 65 | 67 | 72 | 78 |
| 3-Nitro-5-(trifluoromethyl)-$N^1$—(2,2,3,3-tetrafluoropropionyl)-$N^2$—acetyl-o-phenylenediamine | 0.01 | 5 | 5 | 5 | 10 | 12 | 17 | 27 |
| | 0.1 | 0 | 0 | 2 | 3 | 5 | 8 | 15 |
| | 1.0 | 5 | 8 | 10 | 10 | 10 | 12 | 25 |
| Mirex (standard) | 0.01 | 2 | 2 | 3 | 3 | 8 | 18 | 42 |
| | 0.1 | 0 | 0 | 3 | 50 | 67 | 68 | 92 |
| | 1.0 | 0 | 25 | 60 | 100 | | | |
| Soybean Oil (check) | — | 1 | 1 | 2 | 2 | 4 | 12 | 15 |

EXAMPLE 12

3-Nitro-5-(trifluoromethyl)-$N^1$-(2,2,3,3-tetrafluoropropionyl)-o-phenylenediamine was evaluated against laboratory colonies of the red imported fire ant (*Solenopsis invicta*, variety Buron).

The candidate toxicant was formulated at concentrations of 1.0, 2.5, and 5.0% in soybean oil and the resulting formulations were then used to prepare baits containing 30% of one of the respective formulations and 70% pregelled defatted corn grits (on a weight by weight basis). Normal colonies of ants, which had been starved for 5 days, were exposed to the baits for 24–96 hours and then the baits were replaced with the standard laboratory diet. Mortality counts and general observations on the condition of the colonies were recorded weekly. A test was terminated when the queen, brood, and 90% of the workers were dead. Duplicate tests were conducted with each concentration of the candidate toxicant. The results are shown in the following table.

TABLE III

| Concentration of compound in soybean oil | Percent mortality in colony at indicated weeks after initial exposure to bait* | | | | |
|---|---|---|---|---|---|
| | 1 | 2 | 3 | 4 | 8 |
| 1.0 | 95 | 97 | 98 | 99 | D |
| 1.0 | 99 | D | | | |
| 2.5 | 99 | 99 | 99 | D | |
| 2.5 | 99 | D | | | |
| 5.0 | D | | | | |
| 5.0 | D | | | | |
| Check | 0 | 0 | 0 | 1 | 5 |

*D = Death of colony; ants were maintained on the standard laboratory diet following the 24–96 hour exposure to the treated bait.

The foregoing results indicate that the 5.0% concentration killed the colonies within a week. The 2.5% concentration killed 99% of the ants within a week and resulted in the death of 1 colony within 2 weeks and the other colony within 4 weeks. The 1.0% concentration was 95–99% effective within a week and resulted in the death of 1 colony within 2 weeks and the other colony within 8 weeks.

EXAMPLE 13

3-Nitro-5-(trifluoromethyl)-$N^1$-(2,2,3,3-tetrafluoropropionyl)-o-phenylenediamine was formulated in two baits suitable for supplying the compound to ants.

The compound was dissolved in acetone and then in refined soybean oil and the solution was mixed with pregelled defatted corn grits. The acetone was evaporated (a small portion of the 3-nitro-5-(trifluoromethyl)-$N^1$-(2,2,3,3-tetrafluoropropionyl)-o-phenylenediamine crystallized out).

The composition of the resulting baits was as follows:

| | Amount | % of total bait |
|---|---|---|
| Bait #1 = 0.75% | | |
| 3-nitro-5-(trifluoromethyl)-$N^1$—(2,2,3,3-tetrafluoropropionyl)-o-phenylenediamine | 510 grams | 0.75% |
| refined soybean oil | 18.5 kilograms | 27.25% |
| pregelled defatted corn grits | 49 kilograms | 72% |
| Bait #2 = 1.5% | | |
| 3-nitro-5-(trifluoromethyl)-$N^1$—(2,2,3,3-tetrafluoropropionyl)-o-phenylenediamine | 1020 grams | 1.5% |
| refined soybean oil | 18 kilograms | 26.5% |
| pregelled defatted corn grits | 49 kilograms | 72% |

EXAMPLE 14

3-Nitro-5-(trifluoromethyl)-$N^1$-(2,2,3,3-tetrafluoropropionyl)-o-phenylenediamine was also formulated in a 1% bait.

The compound was dissolved in methylene chloride (6 kilograms) and then in refined soybean oil; the solution was added to textured corn grits and the methylene chloride allowed to evaporate prior to use.

The composition of the resulting bait was as follows:

| | Amount | % of total bait |
|---|---|---|
| 3-nitro-5-(trifluoromethyl)-$N^1$—(2,2,3,3-tetrafluoropropionyl)-o-phenylenediamine | 0.3 kilogram | 1% |
| refined soybean oil | 9 kilograms | 30% |
| textured corn grits | 20.7 kilograms | 69% |

EXAMPLE 15

3-Nitro-5-(trifluoromethyl)-$N^1$-(2,2,3,3-tetrafluoropropionyl)-o-phenylenediamine was evaluated against the red imported fire ant (*Solenopsis invicta*) under field conditions. The tests were conducted at three separate locations in Georgia, two with fire ant mounds in coastal variety bermudagrass and the third with fire ant mounds in Pensacola variety Bahiagrass. For all three of the tests, the candidate compound was formulated as described in Example 14. In each test, bait was supplied to five mounds. Visual observation at the time of supplying the bait indicated that the ants accepted the bait immediately. Observations were made on three dates after supplying the bait.

Results were recorded in terms of percent control. The results were as reported in the following tables.

TABLE IV

| Days After Treatment | Percent Control | | |
|---|---|---|---|
| | Adult | Eggs | Larvae |
| Trial 1 (coastal Bermudagrass) | | | |
| 12 | 50 | — | — |
| 47 | 80 | 80 | 80 |
| 74 | 100 | 100 | 100 |
| Trial 2 (coastal Bemudagrass) | | | |
| 13 | 50 | — | — |
| 44 | 80 | both eggs and larvae = 80 | |
| 73 | 100 | 100 | 100 |
| Trial 3 (Pensacola Bahiagrass) | | | |
| 25 | 80 | — | — |
| 41 | 40 | 60 | 60 |
| 70 | 50 | 50 | 50 |

EXAMPLE 16

3-Nitro-5-(trifluoromethyl)-$N^1$-(2,2,3,3-tetrafluoropropionyl)-o-phenylenediamine was evaluated further for the control of the red imported fire ant (*Solenopsis invicta*) under field conditions. The tests were conducted in three different locations in Georgia, and the compound (as a 1% granular formulation prepared as described in Example 14) was applied at each location by a cyclone applicator to an infested plot 210'×210'—at a rate of 0.025 lbs./acre. Three readings were made at each test site, and the results were as follows:

TABLE V

| Days After Treatment | Percent Control | | |
|---|---|---|---|
| | Adult | Eggs | Larvae |
| Trial 1 (coastal Bermudagrass) | | | |
| 12 | 70 | — | — |
| 47 | 60 | 80 | 80 |
| 74 | 95 | 100 | 100 |
| Base colonies = 61/A | | | |
| Trial 2 (coastal Bemudagrass) | | | |
| 13 | 80 | — | — |
| 44 | 80 | both eggs and larvae = 100 | |
| 73 | 95 | 95 | 95 |
| Base colonies = 25/A | | | |
| Trial 3 (Pensacola Bahiagrass) | | | |
| 25 | 80 | — | — |
| 41 | 75 | 90 | 90 |
| 70 | 100 | 100 | 100 |
| Base colonies = 34/A | | | |

EXAMPLES 17–21

Various of the N-(2,2-difluoroalkanoyl)-o-phenylenediamines serving as the present active agent were evaluated as termiticides. The procedure employed was that described by Virgil K. Smith in the *Journal of Economic Entomology*, Vol. 72, No. 6 (December, 1979), page 877 et seq., for a soil toxicity test and a repellency test. Results are reported herein as hours required to control 97% of the termites for the soil toxicity test, and as repellent or not repellent in the repellency test. As reported in the reference, a compound was considered repellent if 21 or more of 30 termites were observed on the untreated soil at all 3 observation times. The results on both tests were as reported in the following table.

TABLE VI

| Compound | Conc. of Compd in ppm | Soil Toxicity Test Hours required to control 97% of test termites | Repellency Test Repellent ("rep") or no repellency ("no rep") |
|---|---|---|---|
| 3-Nitro-5-(trifluoromethyl)-$N^1$—acetyl-$N^2$—(2,2,3,3-tetrafluoropropionyl)-o-phenylenediamine | 1000 | >8 | no rep |
| | 750 | >8 | " |
| | 500 | >8 | " |
| | 250 | >8 | " |
| | 100 | >8 | " |
| | 50 | >8 | " |
| | 25 | >8 | " |
| | 10 | >8 | " |
| | 5 | >8 | " |
| 3-Nitro-5-(trifluoromethyl)-$N^1$—(2,2,3,3-tetrafluoropropionyl)-$N^2$—acetyl-o-phenylenediamine | 1000 | 8 | rep |
| | 750 | 8 | " |
| | 500 | >8 | " |
| | 250 | >8 | " |
| | 100 | >8 | no rep |
| | 50 | >8 | " |
| | 25 | >8 | rep |
| | 10 | >8 | " |
| | 5 | >8 | no rep |
| 3-Nitro-5-(trifluoromethyl)-$N^1,N^2$—bis-(2,2,3,3-tetrafluoropropionyl)-o-phenylenediamine | 1000 | 3 | rep |
| | 750 | 3.5 | " |
| | 500 | 4.5 | " |
| | 250 | 8 | " |
| | 100 | >8 | no rep |
| | 50 | >8 | " |
| | 25 | >8 | " |
| | 10 | >8 | " |
| | 5 | >8 | " |
| 3-Nitro-5-(trifluoromethyl)-$N^1$—(2,2,3,3-tetrafluoropropionyl)-o-phenylenediamine | 1000 | 2 | rep |
| | 750 | 2.5 | " |
| | 500 | 2.5 | no rep |
| | 250 | 4.5 | rep |
| | 100 | >8 | rep |
| | 50 | >8 | no rep |

TABLE VI-continued

| Compound | Conc. of Compd in ppm | Soil Toxicity Test Hours required to control 97% of test termites | Repellency Test Repellent ("rep") or no repellency ("no rep") |
| --- | --- | --- | --- |
| | 25 | >8 | rep |
| | 10 | >8 | rep |
| | 5 | >8 | no rep |
| 3-Nitro-5-(trifluoromethyl)-N$^1$—(pentafluoropropionyl)-o-phenylenediamine | 1000 | 1 | rep |
| | 750 | 1 | " |
| | 500 | 1 | " |
| | 250 | 1.5 | " |
| | 100 | 2 | " |
| | 50 | 3 | no rep |
| | 25 | 4.5 | " |
| | 10 | >8 | rep |
| | 5 | >8 | no rep |

I claim:

1. Method for eradicating a fire ant colony, which comprises supplying to the colony an effective amount of an active agent which is a compound of the formula

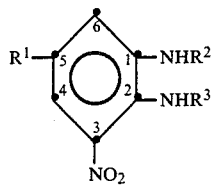

wherein R$^1$ represents
(1) halo,
(2) CF$_3$,
(3) CF$_2$H, or
(4) CF$_2$Cl;
one of R$^2$ and R$^3$ represents a 2,2-difluoroalkanoyl radical of the formula

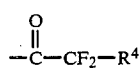

wherein R$^4$ represents
(1) H,
(2) Cl,
(3) F,
(4) difluoromethyl, or
(5) trifluoromethyl;
and the other of R$^2$ and R$^3$ represents
(1) H,
(2) the same 2,2-difluoroalkanoyl radical represented by the first of R$^2$ and R$^3$,
(3) a radical of the formula

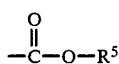

wherein R$^5$ represents loweralkyl of C$_1$–C$_4$ or phenyl,
(4) lower alkanoyl of C$_2$–C$_5$,
(5) benzoyl, or
(6) halogenated lower alkanoyl of C$_2$–C$_5$, subject to the limitation that the alpha position bears at least one substituent selected from the group consisting of hydrogen and halogen of atomic weight from 35 to 127, both inclusive;

subject to the further limitation that when R$^3$ represents a 2,2-difluoroalkanoyl radical, R$^2$ is a group other than H.

2. The method of claim 1 wherein the active agent is a compound of the formula

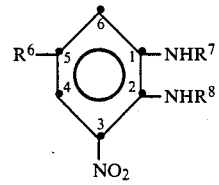

wherein R$^6$ represents chloro or trifluoromethyl; R$^7$ represents a 2,2-difluoroalkanoyl radical as defined in claim 1; and R$^8$ represents H or the same 2,2-difluoroalkanoyl radical represented by R$^7$.

3. The method of claim 2 wherein the active agent is 3-nitro-5-(trifluoromethyl)-N$^1$-(2,2,3,3-tetrafluoropropionyl)-o-phenylenediamine.

4. The method of claim 2 wherein the active agent is 3-nitro-5-(trifluoromethyl)-N$^1$-(pentafluoropropionyl)-o-phenylenediamine.

5. The method of claim 2 wherein the active agent is 3-nitro-5-(trifluoromethyl)-N$^1$,N$^2$-bis(trifluoroacetyl)-o-phenylenediamine.

6. The method of claim 2 wherein the active agent is 3-nitro-5-chloro-N$^1$,N$^2$-bis(trifluoroacetyl)-o-phenylenediamine.

7. The method of claim 2 wherein the active agent is 3-nitro-5-(trifluoromethyl)-N$^1$,N$^2$-bis(2,2,3,3-tetrafluoropropionyl)-o-phenylenediamine.

* * * * *